United States Patent [19]
Brown

[11] 3,945,241
[45] Mar. 23, 1976

[54] FRETTING CORROSION TEST FIXTURE

[75] Inventor: Stanley R. Brown, Doylestown, Pa.

[73] Assignee: The United States of America as represented by the Secretary of the Navy, Washington, D.C.

[22] Filed: Mar. 18, 1975

[21] Appl. No.: 559,604

[52] U.S. Cl. ............................. 73/7; 73/15.6
[51] Int. Cl.² ................................. G01N 3/56
[58] Field of Search ............ 73/7, 9, 10, 15.6, 101

[56] References Cited
UNITED STATES PATENTS

| | | | |
|---|---|---|---|
| 2,969,669 | 1/1961 | Hirschhorn | 73/7 |
| 3,033,019 | 5/1962 | Oliver | 73/9 |
| 3,221,534 | 7/1965 | Alfred et al. | 73/7 |
| 3,751,977 | 8/1973 | Schilling, Jr. | 73/15.6 |

OTHER PUBLICATIONS
Toth "The Investigation of the Steady Stage of Steel Fretting" in Wear, Vol. 20, No. 3, 1972, pp. 277–286.

Primary Examiner—Herbert Goldstein
Attorney, Agent, or Firm—R. S. Sciascia; Henry Hansen

[57] ABSTRACT

A fretting corrosion test fixture for evaluating materials or coatings in variable temperature environments and having a load bar and a flexure bar rigidly mounted at their respective one ends in the jaws of a vise and separated by a shim of selected thickness. The load and flexure bars are cantilevered out from the vise, the other end of the flexure bar being connected to an eccentric drive assembly for deflecting the flexure bar. A pair of material specimens having a combined thickness equal to that of the shim are attached, respectively, near the end of the load bar and intermediate the ends of the flexure bar and in contact with each other. A cylindrical furnace is mounted for enclosing the specimens for high temperature evaluation. Fretting corrosion is produced on the attached fretting specimens under controlled conditions by deflecting the flexure bar a predetermined amount resulting in relative movement and load at the interface of the specimens.

10 Claims, 6 Drawing Figures

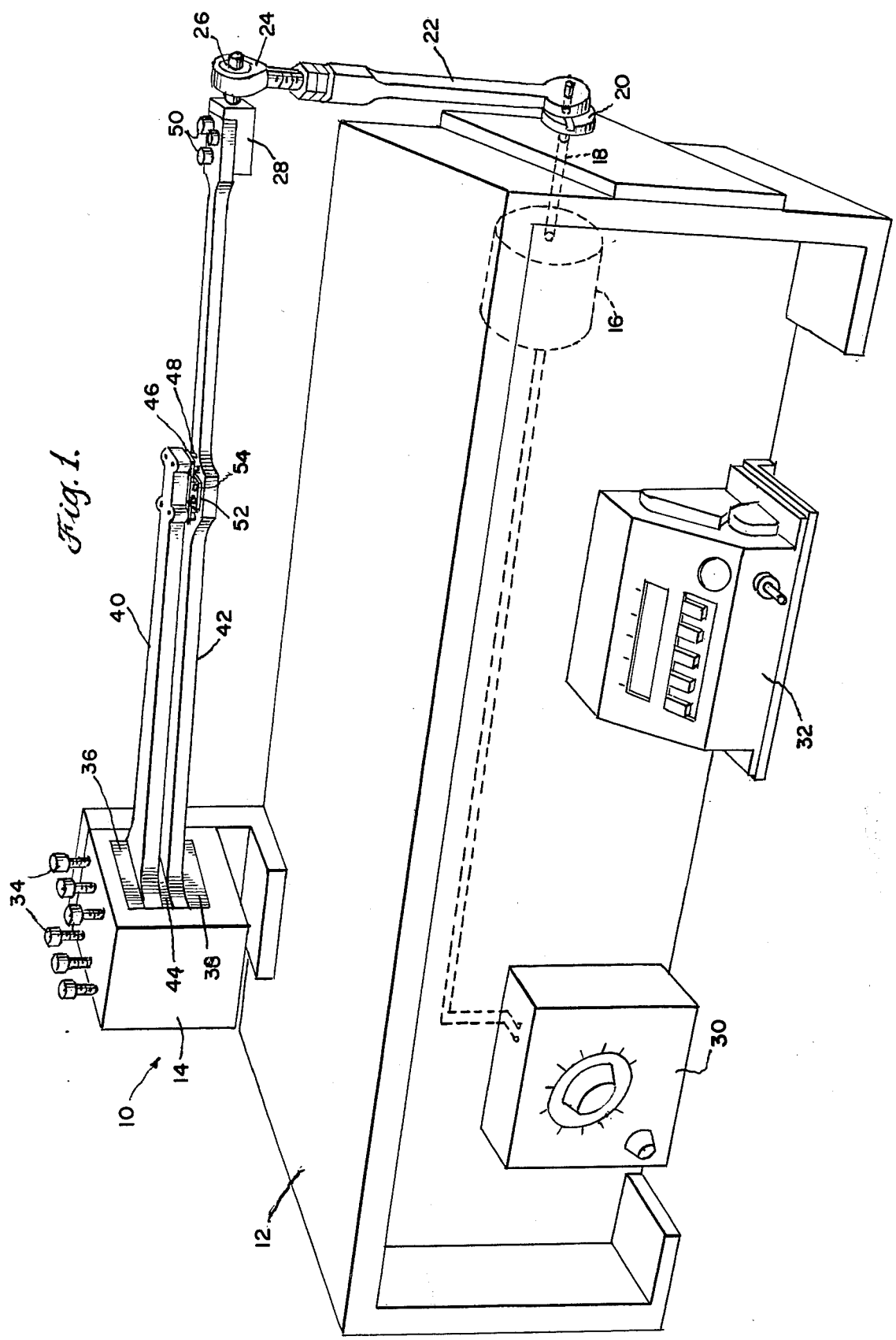

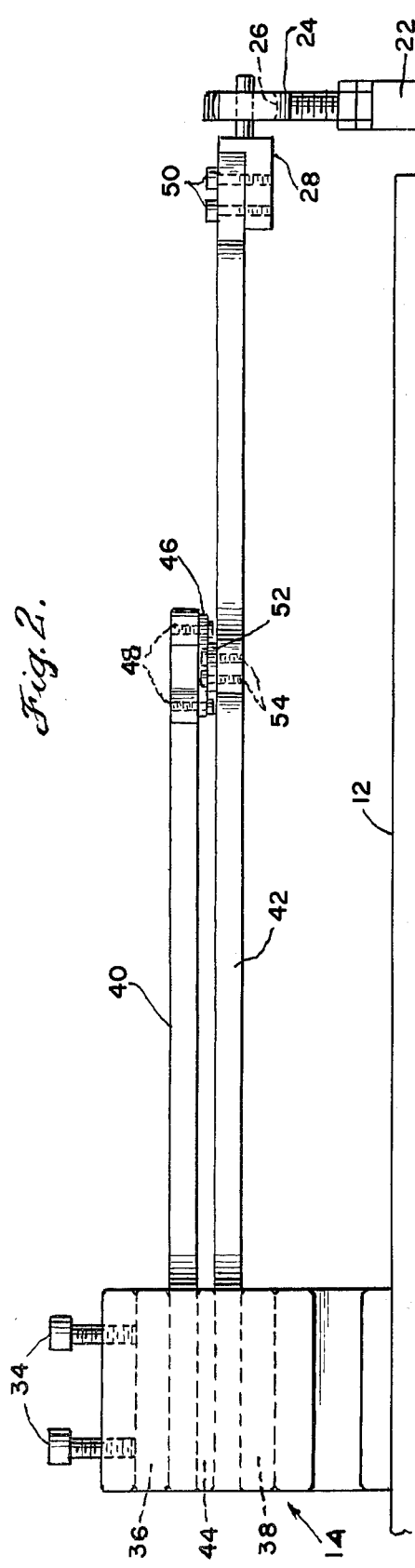
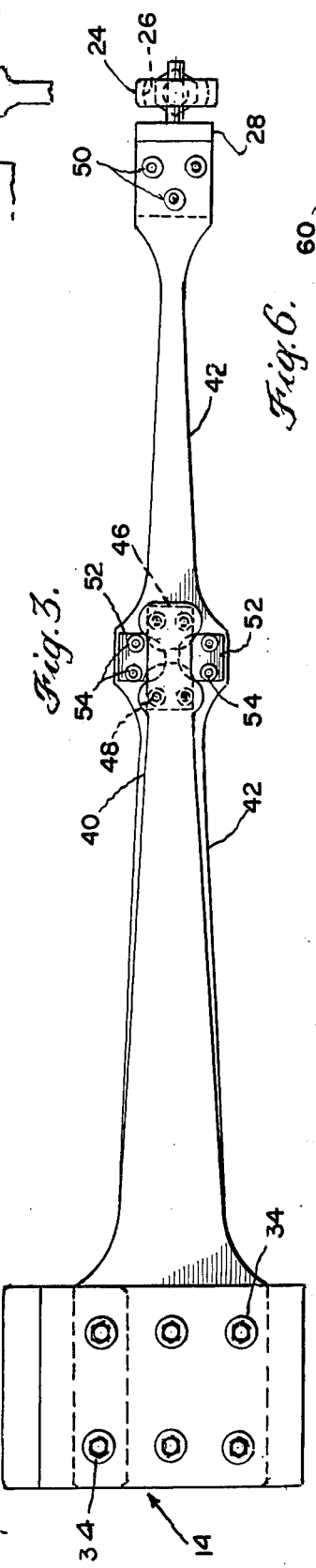
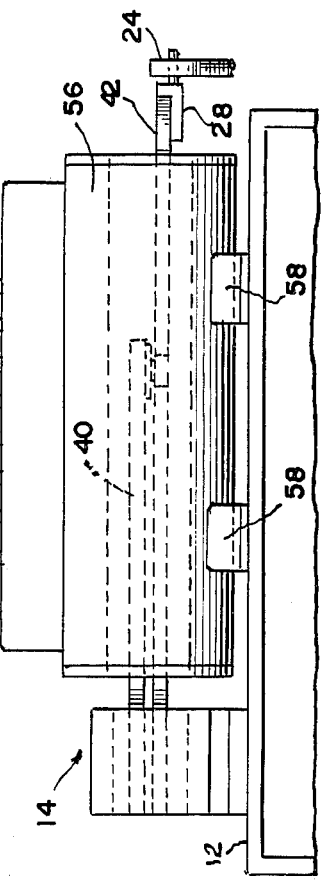
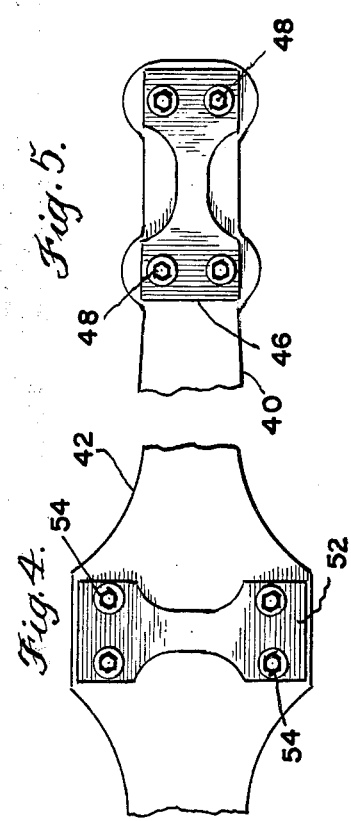

3,945,241

FRETTING CORROSION TEST FIXTURE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates generally to material and coating test fixtures and particularly to a fretting corrosion test fixture.

Fretting describes corrosion damage occurring at contact areas between materials under load subjected to small relative movement or slip. The fretting corrosion damage appears as pits or grooves in the metal surrounded by corrosion debris and is also known as friction oxidation, wear oxidation, chafing, and false brinelling. Fretting has been observed at the interface of metallic joints in engine components, automotive parts and airframe structures. Fretting corrosion is very detrimental because of the destruction of metallic components and the formation of oxide and metallic particulate. Frequently, the result is a loss of tolerances and loosening of mating parts. Further, fretting causes fatigue fractures since the loosening of components permits excessive strain, and the pits formed by fretting act as stress-raisers.

The basic requirements for the occurrence of fretting corrosion are:

1. The interface must be under load;
2. Vibration or repeated relative motion between the two surfaces must occur; and
3. The load and the relative motion of the interface must be sufficient to produce slip or deformation on the surfaces.

Methods and fixtures for performing fretting corrosion studies primarily involve lubrication wear equipment. One other method of inducing fretting corrosion wear is to alter fatigue testing equipment by applying normal loads to induce fretting fatigue. Testing in high temperature environments often require complex and relatively expensive test fixtures not readily adaptable for placing test specimens within a high temperature environment.

SUMMARY OF THE INVENTION

Accordingly, it is an object of the present invention to provide a fretting corrosion test fixture which localizes fretting action so as to make it easily accessible to high temperature studies. Another object is to provide a fretting corrosion test fixture which utilizes conveniently replaceable fretting specimens whose size and shape can be readily modified for the application of differing flexure loads. Yet another object is to provide a relatively simple and inexpensive fretting corrosion test fixture.

Briefly, these and other objects are accomplished by a fretting corrosion test fixture which evaluates materials or coatings in variable temperature environments. The test fixture of the present invention has a load bar and a flexure bar rigidly mounted below the load bar at their respective one ends in the jaws of a vise wherein the bars are separated by a shim of selected thickness in the jaw area. The load and flexure bars are cantilevered out from the vise, the other end of the flexure bar being connected to an eccentric drive assembly for deflecting the flexure bar. A pair of fretting specimens having a combined thickness equal to that of the shim are attached, respectively, to the end of the load bar and intermediate the ends of the flexure bar and in surface contact with each other. A cylindrical furnace is mounted on the test fixture for enclosing the specimens to provide high temperature fretting corrosion evaluation. Fretting corrosion is produced by repetively deflecting the flexure bar a predetermined amount resulting in relative movement and load at the interface of the specimens. The specimens are easily replaceable on both the load and flexure bars and readily modified as to size and shape for applying differing fretting loads.

For a better understanding of these and other aspects of the invention, references may be made to the following detailed description taken in conjunction with the accompanying drawings.

BRIEF DESCRIPTION OF THE DRAWINGS

FIG. 1 is a perspective view of a fretting test fixture constructed in accordance with the invention;

FIG. 2 is a side elevational view of a portion of the fixture shown in FIG. 1;

FIG. 3 is a plan view of FIG. 2;

FIG. 4 is an enlarged fragmentary plan view of the specimen holding portion of the flexure bar;

FIG. 5 is an enlarged and inverted fragmentary plan view of the specimen holding portion of the load bar; and FIG. 6 is an elevational view illustrating the application of a furnace to the test fixture shown in FIG. 1.

DESCRIPTION OF THE PREFERRED EMBODIMENT

Referring now to FIG. 1, there is shown a perspective view of a fretting test fixture 10 constructed in accordance with the present invention. A table 12 has a top surface having a vise 14 rigidly attached thereto. A motor 16 is positioned under the top surface of the table 12 and has an output shaft 18 connected to an eccentric drive assembly. The eccentric drive assembly comprises a variable eccentric disc 20 connected to the end of the output shaft 18 and positioned exterior to one end of the table 12, a cranking arm 22 connected at one end to the disc 20, an adjustable crank end 24 having a radial bearing insert 26, and a clamp 28 connected to the bearing 26. A motor speed control 30 is securably attached to a front panel of the table 12 and is electrically connected to the motor 16. A counting device 32 is also securably attached to the front panel of the table 12 and is connected to the eccentric drive assembly in any convenient manner such as, for example, a switching mechanism or a photocell detector which indicates the strokes produced by the crank arm 22. The vise 14 comprises a plurality of clamping screws 34, an upper jaw 36, and a lower jaw 38. Intermediate the jaws 36, 38 and shown clamped in the vise 14 is a load bar 40 adjacent the upper jaw 36, a flexure bar 42 adjacent the lower jaw 38, and a shim 44 intermediate the load bar 40 and the flexure bar 42. A first fretting specimen 46 is securably attached by screws 48 to the free floating cantilevered end of the load bar 40. The end of the flexure bar 42 that is pointing away from the vise 14 is securably attached to the clamp 28 by a plurality of screws 50. Intermediate the ends of the flexure bar 42 and adjacent the specimen 46 is a second fretting specimen 52 placed in orthogonal alignment to the first specimen 46 and securably attached to the flexure bar 42 by a plurality of screws 54.

Referring now to FIG. 2, there is shown a side elevational view of the test fixture shown in FIG. 1. The clamping screws 34 produce a downward force on the upper jaw 36 which compressively holds the load bar 40, the shim 44, and the flexure bar 42 adjacent the lower jaw 38.

More clearly indicated is the positioning of the first specimen 46 secured to the end of the load bar 40 by the screws 48, and the second specimen 52 in surface contact with the first specimen 46 and attached intermediate the ends of the flexure bar 42 by screws 54. Also shown in greater detail is the crank end 24 having threads at the end thereof which engage with the top portion of the cranking arm 22 so as to shorten or lengthen the effective length thereof.

Referring now to FIG. 3, there is shown a top plan view of that portion of the test fixture shown in FIG. 2. The load arm 40 is shown extended in a cantilevered fashion from the vise 14 and having a triangulated shape with a varying width somewhat smaller than the width of the underlying flexure bar 42 which is also triangular in shape. Both the bars 40, 42 are preferably triangularly shaped because of the more uniform absorption and application of load stress known to be associated with this configuration. The respective widths and thicknesses of the bars 40, 42, however, may be suitably enlarged or diminished to reflect the designers choice of more or less rigidity or surface area. More clearly shown is the positioning of the first specimen 46 in longitudinal alignment with the length of the load bar 40. Also more clearly shown is the positioning of the second specimen 52 in orthogonal alignment with the first specimen 46 and secured to the flexure bar 42 intermediate the ends thereof.

FIG. 4 shows an enlarged fragmentary plan view of the specimen holding portion of the flexure bar 42 and more clearly illustrates one possible shape of the second specimen 52. In this example, the specimen 52 has been narrowed at the mid section thereof to provide a predetermined sample cross-sectional area which can readily be altered as to thickness, length and width. The specimen 52 may also be readily removed and replaced upon the bar 42 by the removal of the screws 54.

FIG. 5 is an enlarged and inverted plan view of the specimen holding portion of the load bar 40. Similar to the view shown in FIG. 4, the specimen 46 is securably attached to the end of the bar 40 by the screws 48 which permit ready removal and replacement of the specimen. Similar to the specimen shown in FIG. 4, specimen 46 is also illustrated by way of example as having a modified cross-sectional area which may be easily formed to provide different thicknesses, lengths, or widths. That portion of the load bar 40 underlying the area about each of the screws 48 is shown having an arc-like contour due to the desirability of providing sufficient bar strength about the threaded holes adapted to receive the screws 48. Although in the example of the foregoing embodiment, the specimens 46, 52 are shown placed, respectively, on load bar 40 and flexure bar 42 in an orthogonal arrangement, the specimens may just as easily be placed in any other convenient arrangement which will achieve the desired load stresses and relative motion between the interface of the contact surfaces of the specimens.

FIG. 6 illustrates an elevational view of a second embodiment of the present invention showing the application of a furnace 56 to the test fixture 10. The furnace 56 forms a heated cylinder which encloses the load bar 40, the flexure bar 42, and the mounted specimens 46, 52. Appropriate openings are provided at the respective ends of the furnace 56 to accomodate the bars and also to provide for the necessary freedom of movement of the bars during testing operations. The furnace 56 is attached to the top surface of the table 12 by a pair of supports 58. A plurality of tapping terminals 60 are provided at the top of the furnace 56 and are adapted to receive electrical energy which will heat the furnace. Temperature control is maintained within the furnace 56 by activating one or more of the appropriate terminals 60 to produce the desired amount of heat.

Referring now to FIGS. 1–5, the operation of the present invention will now be explained. Fretting specimens of the particular material that is desired to be tested such as, for example, titanium are machined to their desired shape and thickness. The machined specimens may be of equal thickness and are modified as shown in FIGS. 4 and 5 to include a predetermined cross sectional area when the specimens are mated in the test fixture. The specimens selected may also be constructed of different materials such as one from titanium sheet and one from aluminum sheet for evaluating a titanium-aluminum interface. Once the type of material and the shape of material are selected for the specimens, the shim 44 is sized to have a thickness equal to the combined thicknesses of the specimens 46, 52. Each of the specimens 46, 52 are attached, respectively, to the load bar 40 and the flexure bar 42 in the manner shown in the drawings. The load bar 40, the selectively sized shim 44, and the flexure bar 42 are then clamped in the vise 14 by the screws 34. The other end of the flexure bar is then connected to the clamp 28 by means of the screws 50. During the actual testing operation by the fixture 10, it is necessary that opposing load forces be applied in a normal direction to each of the specimen surfaces and at the interface thereof. In addition, it is also necessary that relative movement or slip amplitude occur at the interface of the specimens 46, 52 thereby producing a fretting corrosion effect. Accordingly, the thickness, length, and materials comprising the bars 40, 42 are preselected to set up initial testing conditions as to the stresses and loading forces to be applied to the specimens during the test. Moreover, the eccentricity of the cranking arm 22 will be adjusted to provide the desired degree of reciprocating stroking action and consequential flexing of the flexure bar between the vise 14 and the clamp 28. The eccentricity of the flexing stroke as produced at the cranking arm 22 is most easily adjusted in a conventional manner by moving the end of the arm 22 either nearer to or farther from the center of the disc 20 as permitted by a diametrical slot milled in the disc 20 and securing a bolt thereby which forms an axle for the end of the arm 22. Having secured the specimens to the respective bars and tightened the vise 14, an adjustment is made so as to provide for zero spacing between the specimens 46, 52 when the cranking arm 22 is at the lowermost position of its stroke. This adjustment is most easily accomplished by manually placing the cranking arm at the lowermost stroke position and by adjusting the screw threads at the end of the arm end 24 so as to provide minimal surface contact at the specimens interface. Accordingly, it is intended in the present invention that after the foregoing adjustment has been made, the test specimens shall always be in contact with each other during the test operation and, consequently, have a compressive load applied at the interface surfaces during the entire period of the test. The applied load, however, will alternately increase and decrease in a sinusoidal fashion according to the position of the flexing stroke.

To start the test procedure, the motor 16 is activated by the speed control 30 to provide a desired rpm output at the shaft 18 which rpm will coincide with the frequency of the flexing action produced in the load bar 40 and flexure bar 42. As the reciprocating cranking arm 22 begins its upward stroke the flexure bar is flexed toward and against the load bar in a plane formed by the longitudinal axes of both bars. Both the flexure and load bar bend in an upward direction with the result that the specimens 46, 52, which are secured to the respective bars, begin to move relative to each other with a shear-like motion. The relative distance over which the specimens move is known as the slip amplitude. The opposing loads produced by the flexing load bar 40 and the flexure bar 42 at the interface of the specimens while testing titanium materials, for example, have resulted in normal load forces of up to 850 psi, while the slip amplitude at the interface of the titanium specimens has been approximately 0.001 inch. The counter 32 is conveniently employed to count the number of strokes or flexures at the specimens interface and produces an accurate indication of the number of fretting strokes to which the specimens have been subjected during the test.

Referring now to FIG. 6 there is shown a second embodiment of the present invention in which a cylindrical furnace 56 is mounted on the test fixture table 12 by means of supports 58 to enclose portions of the bars 40, 42 as well as the secured specimens 46, 52. In operation, the furnace is heated to a temperature which is controlled and selected by application of an electrical power source to one or more of the terminals 60 provided at the top of the furnace 56. Each of the terminals 60 are connected in a conventional manner to various portions of a heating element (not shown) within the furnace 56. The furnace 56 is sufficiently sealed at the respective ends thereof to contain the heat but provides for openings sufficient to pass the bars 40, 42 and allow for unrestricted flexing movement. As is well known in the art, fretting corrosion will vary with increased temperatures and it is desirable to examine the effects of such corrosion upon appropriate specimens at a variety of temperature environments. This embodiment of the present invention thus provides a convenient method of enclosing the test specimens within a high temperature environment, all of which is done in a work area which is easily accessible to the test operator.

Test specimens other than metal such as plastics, coatings, or lubricants are easily adaptable for use within the present invention. At the end of the test of such specimens, fretting corrosion may be evaluated by noting the amount and composition of debris produced by the test or by other testing standards such as the reduced weight or volume of the test specimens.

Thus it may be seen that there has been provided a novel fretting corrosion test fixture which generates a corrosive action upon a variety of test materials and which testing may be conveniently accomplished in high temperature environments.

Obviously, many modifications and variations of the invention are possible in light of the above teachings. It is therefore to be understood that within the scope of the appended claims the invention may be practiced otherwise than as specifically described.

What is claimed is:

1. A test fixture for fretting corrosion testing of first and second material specimens, comprising in combination:
   clamping means;
   a flexure bar fixed at one end in said clamping means and formed to secure the first specimen intermediate the ends thereof;
   a load bar fixed at one end in said clamping means parallel to said flexure bar and formed to secure the second specimen near the other end thereof and in abutment with the first specimen; and
   force exerting means connected to the other end of said flexure bar for producing a reciprocating force thereon in the plane formed by the respective longitudinal axes of said flexure and said load bars, said force exerting means including an adjustable means for maintaining a compressive load applied at the specimen interface surface during the application of said reciprocating force.

2. A fretting corrosion test fixture according to claim 1 further comprising:
   a shim fixed in said clamping means and positioned intermediate the fixed ends of said flexure bar and said load bar, said shim having a thickness equal to the combined thicknesses of the first and second specimens between said bars for providing a predetermined spacing between said bars.

3. A fretting corrosion test fixture according to claim 2 wherein said force exerting means further comprises:
   motor means; and
   an eccentric drive assembly drivingly connected between said flexure bar and said motor means for producing said reciprocating force.

4. A fretting corrosion test fixture according to claim 3 wherein said flexure bar is triangular in shape having at said other end an apex engaged by said eccentric drive assembly and at said one end a base fixed in said clamping means.

5. A fretting corrosion test fixture according to claim 3 wherein said load bar is triangular in shape having at said other end an apex formed to secure the second specimen and at said one end a base fixed in said clamping means.

6. A test fixture for fretting corrosion testing of first and second material specimens in a variable temperature environment, comprising in combination:
   clamping means;
   a flexure bar fixed at one end in said clamping means and formed to secure the first specimen intermediate the ends thereof;
   a load bar fixed at one end in said clamping means parallel to said flexure bar and formed to secure the second specimen near the other end thereof and in abutment with the first specimen;
   force exerting means connected to the other end of said flexure bar for producing a reciprocating force thereon in the plane formed by the respective longitudinal axes of said flexure and said load bars, said force exerting means including an adjustable means for maintaining a compressive load applied at the speciment interface during the application of said reciprocating force; and
   heating means enclosing said load bar and said flexure bar intermediate said clamping means and said force exerting means for increasing the environmental temperature about the first and second specimens.

7. A fretting corrosion test fixture according to claim 6 further comprising:
a shim fixed in said clamping means and positioned intermediate the fixed ends of said flexure bar and said load bar, said shim having a thickness equal to the combined thicknesses of the first and second specimens between said bars for providing a predetermined spacing between said bars.

8. A fretting corrosion test fixture according to claim 7 wherein said force exerting means further comprises:
motor means; and
an eccentric drive assembly drivingly connected between said flexure bar and said motor means for producing said reciprocating force.

9. A fretting corrosion test fixture according to claim 8 wherein said flexure bar is triangular in shape having at said other end an apex engaged by said eccentric drive assembly and at said one end a base fixed in said clamping means.

10. A fretting corrosion test fixture according to claim 8 wherein said load bar is triangular in shape having at said other end an apex formed to secure the second specimen and at said one end a base fixed in said clamping means.

* * * * *